United States Patent [19]

Jackson

[11] Patent Number: 5,720,751

[45] Date of Patent: Feb. 24, 1998

[54] TOOLS FOR USE IN SEATING SPINAL RODS IN OPEN ENDED IMPLANTS

[76] Inventor: Roger P. Jackson, 4706 W. 86th St., Prairie Village, Kans. 66207

[21] Appl. No.: 757,483

[22] Filed: Nov. 27, 1996

[51] Int. Cl.⁶ .................................................. A61B 17/88
[52] U.S. Cl. ........................... 606/86; 606/99; 606/104; 606/61; D24/133; D24/143
[58] Field of Search ........................... 606/61, 104, 60, 606/99, 86

[56] References Cited

U.S. PATENT DOCUMENTS 5,020,519   6/1991   Hayes et al. ............................ 606/237

OTHER PUBLICATIONS

Surgical techniques literature of Sofamor Danek the Spine Specialist entitled *Pedicle Screw Spinal System*, pp. 4 and 22 exact publication date unknown, but believed to be 1995.

*Primary Examiner*—Michael Buiz
*Assistant Examiner*—David O. Reip
*Attorney, Agent, or Firm*—Litman, McMahon & Brown, L.L.C.

[57] ABSTRACT

A set of tools for use in seating a spinal rod in a rod receiving channel in a head of an open ended spinal surgery implant such as a bone screw, hook or transverse connector wherein each of the tools comprises an implant holder for grasping, holding or engaging an implant, and a pusher assembly including a pusher bar advanceable relative to the implant holder to drive, push or force a spinal rod into the rod receiving channel of an implant held by the implant holder. The implant holders are of various configurations to facilitate holding or grasping of different types of implants or to accommodate different situations relating to the location of the implant. The pusher assembly is adapted for interchangeable use with each of the various implant holders. The pusher assembly is threadingly secureable to each of the implant holders and includes a pusher bar having an elongate slot extending therethrough. The slot in the pusher bar and a channel or slot in the implant holder provides access to the head of the open ended implant in which the spinal rod is seated to permit the installation of a cap thereon.

20 Claims, 6 Drawing Sheets

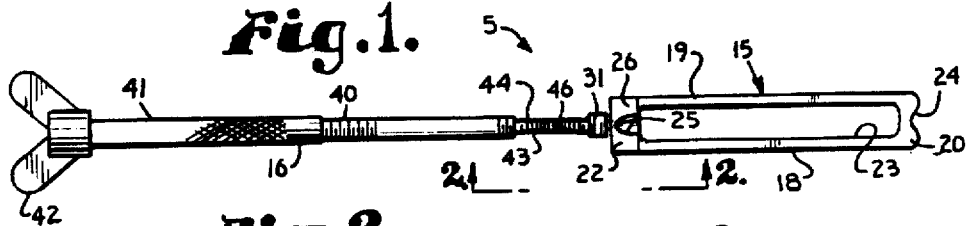
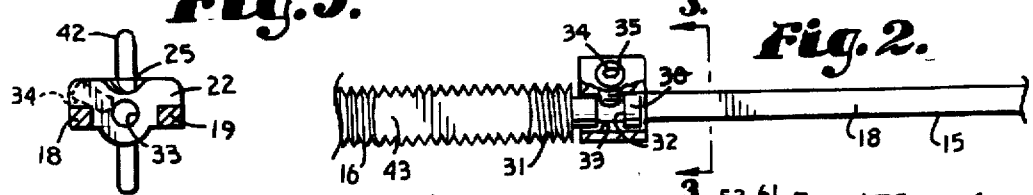
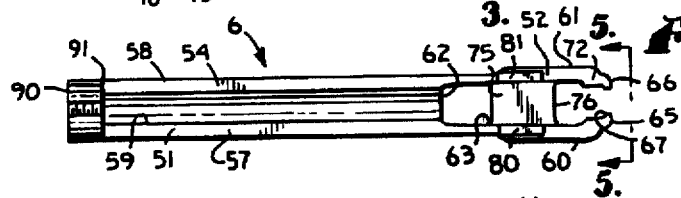
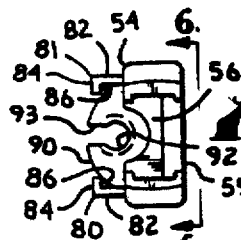
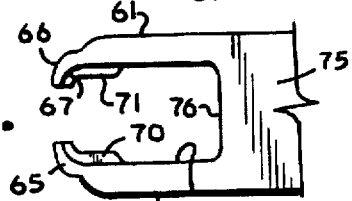
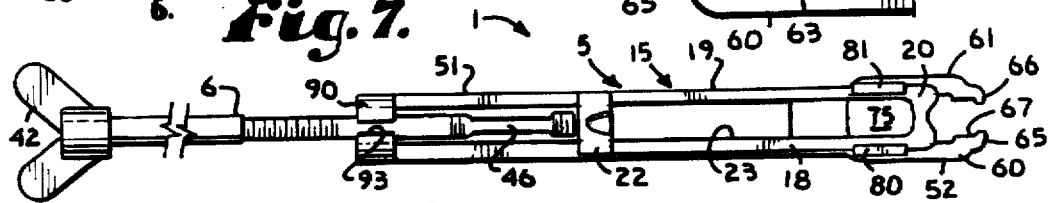
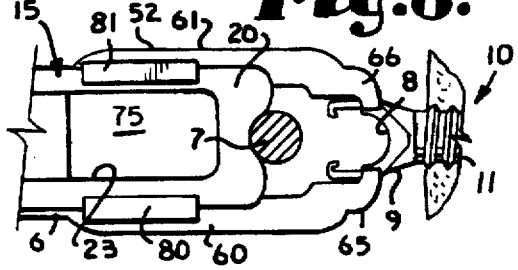
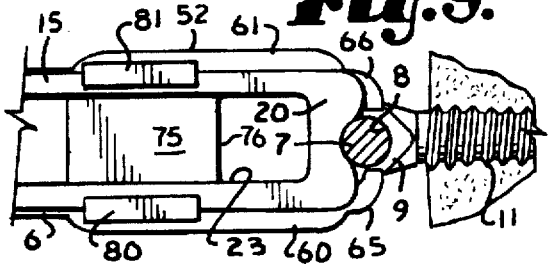

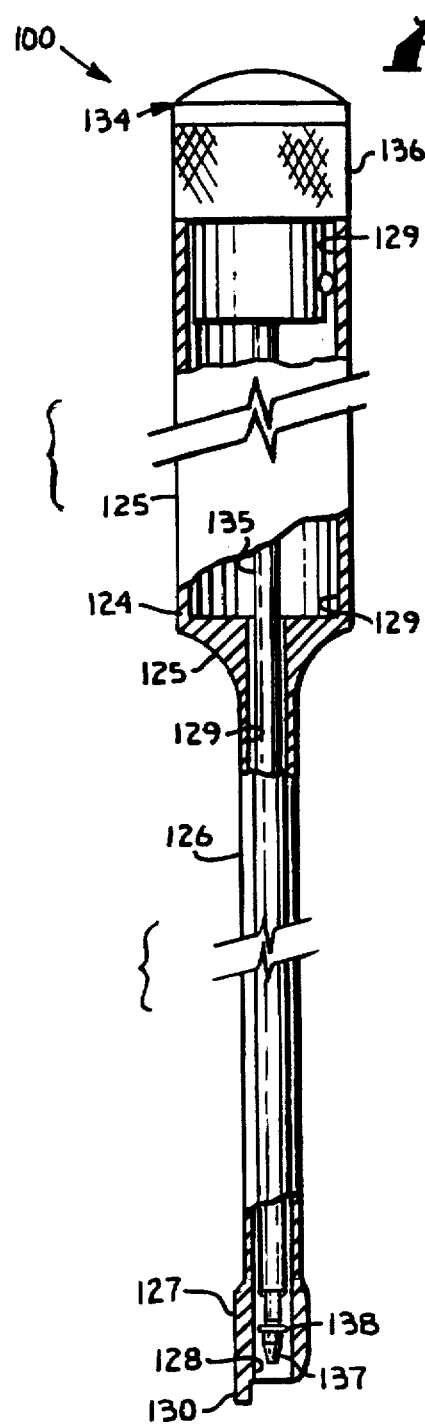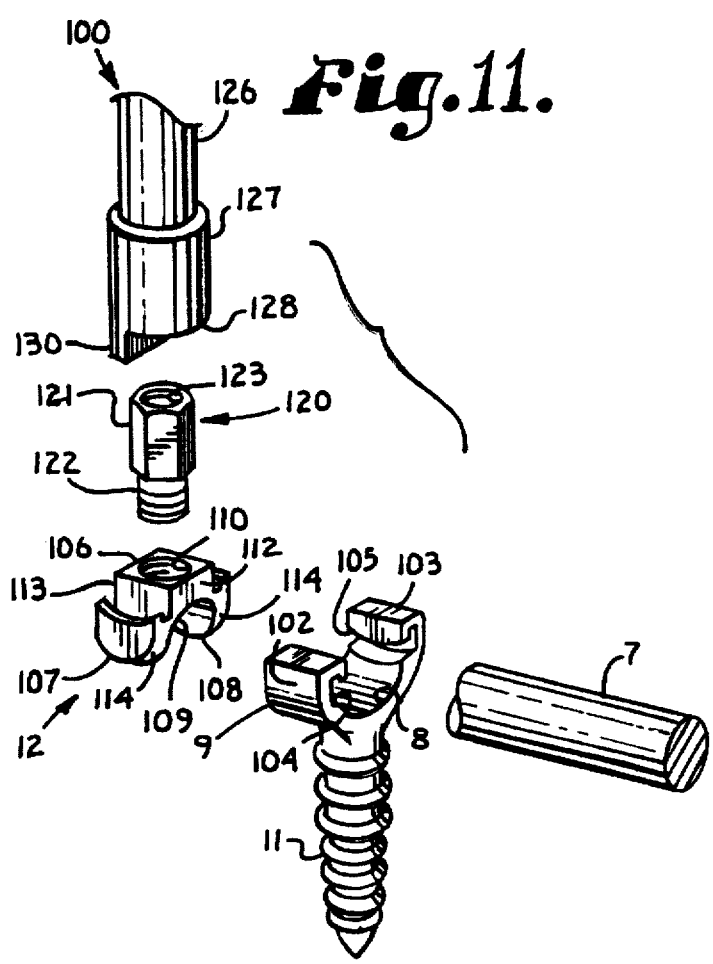
Fig. 10.
Fig. 11.

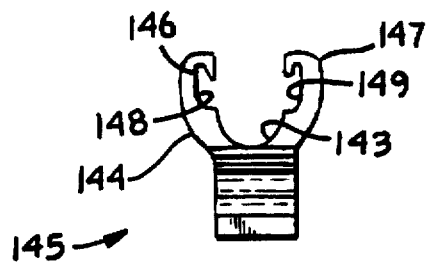
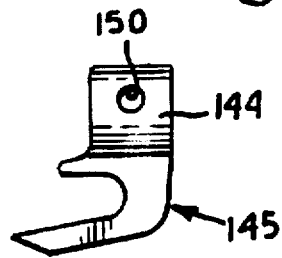
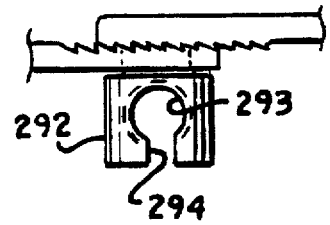
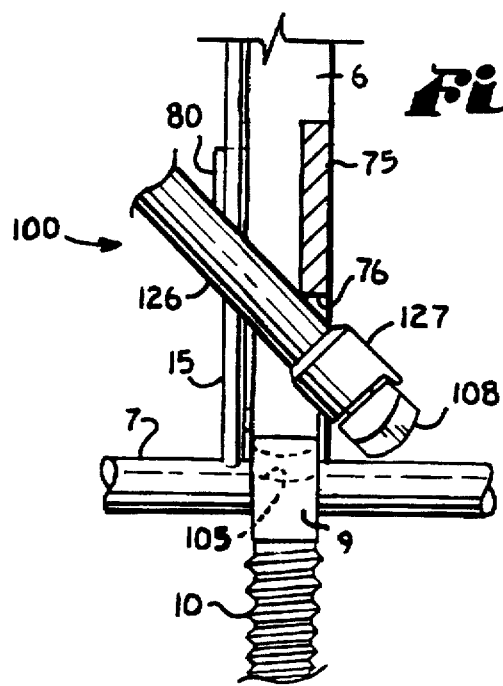
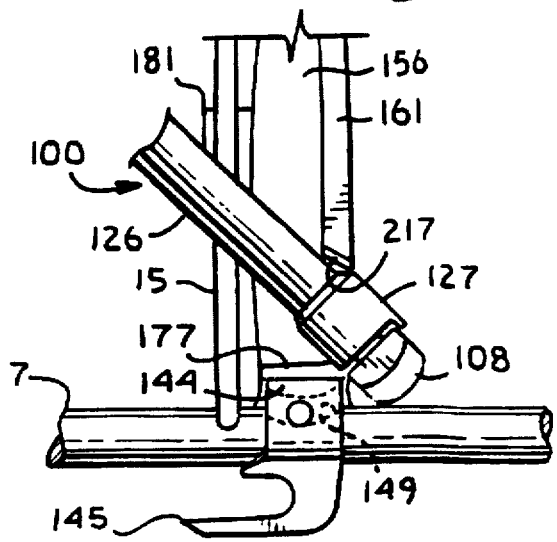

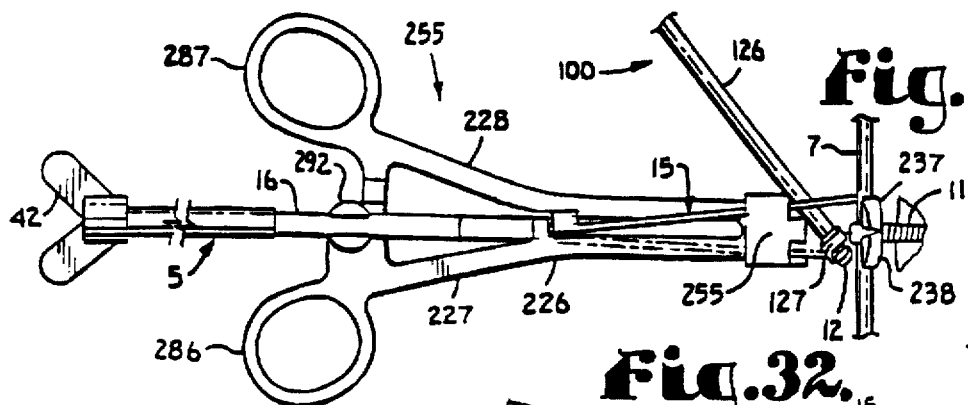
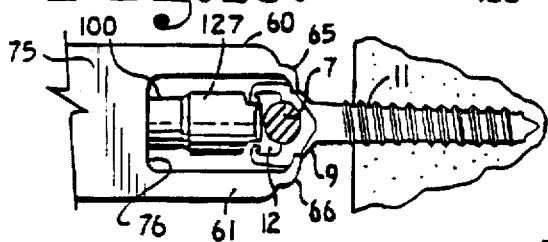
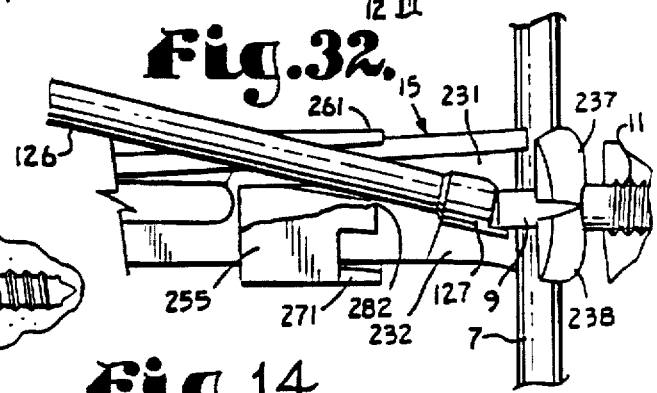
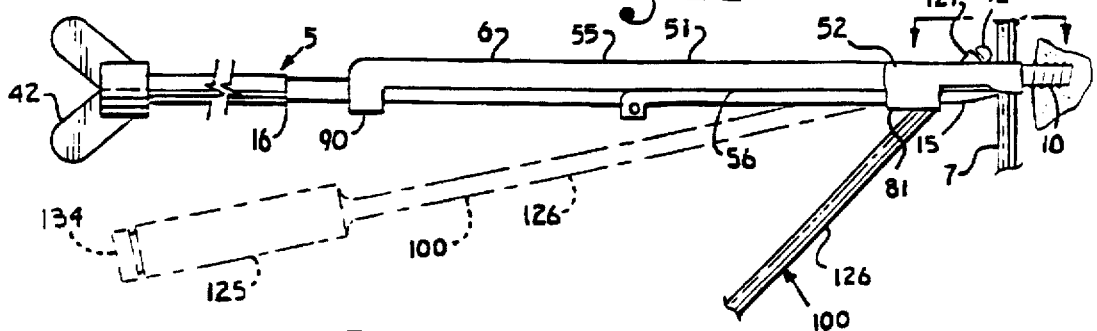
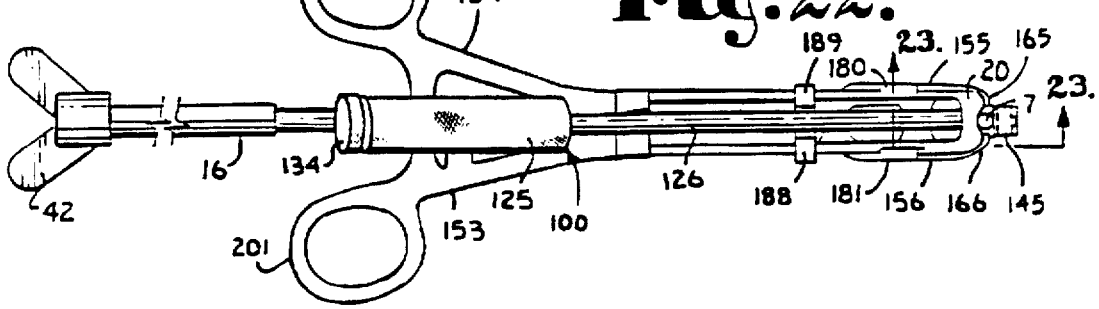

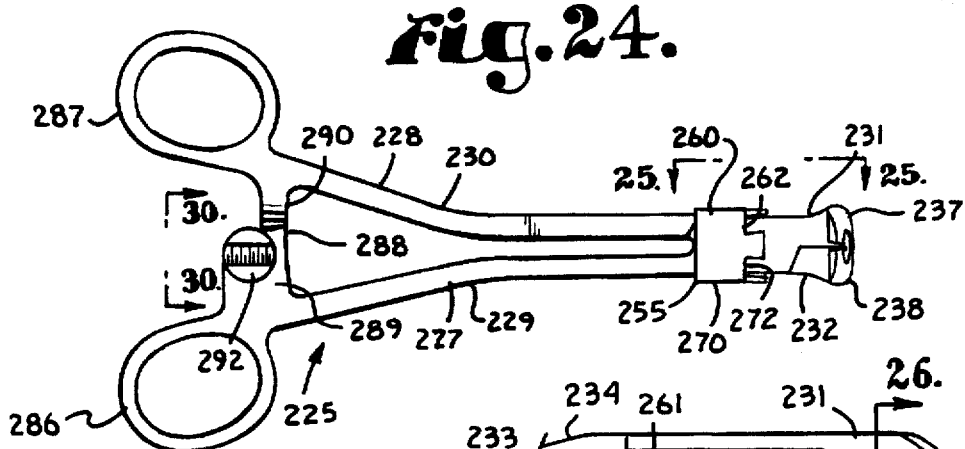
Fig. 24.
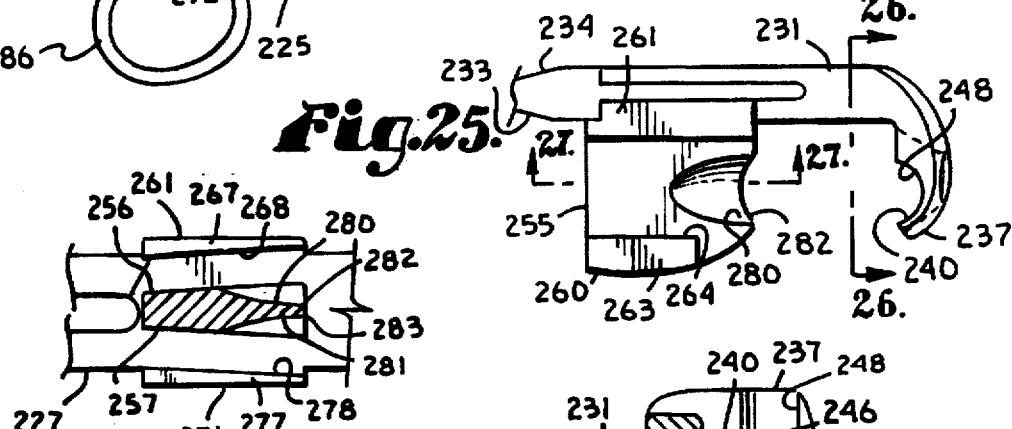
Fig. 25.
Fig. 27.
Fig. 26.
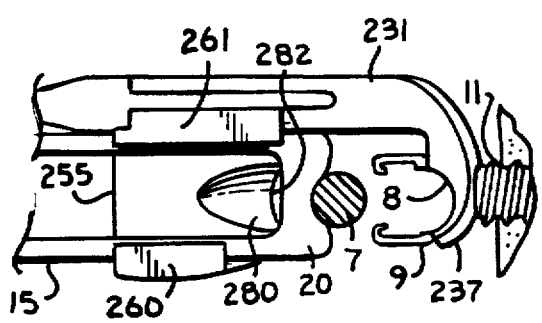
Fig. 28.
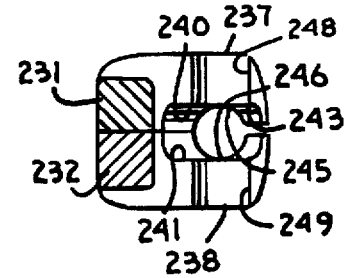
Fig. 29.

TOOLS FOR USE IN SEATING SPINAL RODS IN OPEN ENDED IMPLANTS

BACKGROUND OF THE INVENTION

The present invention relates to tools for use in surgically installing apparatus for correcting orthopedic deformities in a patient and, in particular, to tools specifically designed to facilitate alignment of or seating of spinal rods within open ended implants and which also facilitate closing off or capping the open ended implant while maintaining the proper orientation of the spinal rod with the open ended implant. The tools of the present invention allow a surgeon to push or translate a rod toward and into an open end of one or more implants and/or to pull or translate one or a group of spinal bones toward the rod such that open ends of implants in the bones receive the rod.

Spinal osteosynthesis apparatus generally comprises a rod or system of rods which are secured along at least a portion of the spine by bone screws, including sacral screws and pedicle screws, transverse connectors and bone hooks for stabilizing and adjusting spinal alignment. The bone screws, transverse connectors, bone hooks and related items which are intended for use in connecting the rods to the bone and to facilitate adjustment of the rods may collectively be referred to as hardware or implants. In a very basic apparatus, the bone screws have a spinal rod receiving bore extending through a ring or head of the screw. The screws are secured in the vertebra at desired locations and a spinal rod is then extended through the spinal rod bore in each bone screw. Set screws, inserted in threaded bores extending through the wall of the screw ring, preferably perpendicular to the axis of the spinal rod bore, are tightened to fix the translational and rotational relationship of the rods within the bores. The rods may then be bent or formed to support the spine in a desired manner or to exert the desired corrective or stabilizing forces on the spine.

A slightly more complicated system uses transverse connectors in association with the bone screws to secure the spinal rods. The transverse connectors include an arm and a head. The head has a spinal rod bore extending therethrough and the arm is normally equivalent in diameter to the spinal rod. The arm of the connector is inserted through the spinal rod bore in the pedicle screw then the spinal rod may be inserted through the spinal rod bore in the transverse connectors. A threaded bore extends through the head of the connector perpendicular to the axis of the spinal rod bore. Once the rod is inserted through the bore in the transverse connectors, a set screw is inserted through the threaded bore in each connector and tightened to fix the relative position of the rod within the spinal rod bore. Similarly a set screw is inserted in a threaded bore in the head of each pedicle screw and tightened to fix the position of the transverse connector with respect to the pedicle screws.

The pedicle screws, transverse connectors, bone hooks or related implants or hardware may be of the closed end type as discussed above or of an open end type wherein the head of the screw or connector generally incorporates a U-shaped channel or groove, an upper end of which may be closed off by a cap or saddle to form the spinal rod bore. The threaded set screw bore typically extends through the cap. With open end type implants, the spinal rod may be inserted from above, into the U-shaped channel instead of having to insert the spinal rod axially through the rod receiving bores of closed end type implants.

As noted previously, the spinal rods are generally bent or shaped to exert the desired corrective forces on the spine to realign the spine. Therefore, to obtain the desired alignment, the rod and the open ended implants often must be forced into alignment by generally driving the rod and the U-shaped channel of an open ended implant toward one another. Once the rod is seated in the open ended implant, the implant must be capped or closed off to secure the rod thereto.

Devices have been developed for driving spinal rods into alignment with implants, such as the Offset Mini-Corkscrew sold by Sofamor Danek used in combination with a Central Post Hook Holder or Hook/Screw Holder also sold by Sofamor Danek. This combination of tools is used to drive a spinal rod having connectors secured thereto into alignment with an open ended pedicle screw adapted to receive a portion of the connector such that the rod may be secured to the pedicle screw via the connector.

The Offset Mini-Corkscrew and Hook/Screw Holder are not adapted for use in seating a spinal rod within the U-shaped channel of an implant such as a pedicle screw. Use of the Offset Mini-Corkscrew and Hook/Screw Holder to do so would be impractical in that once the rod was seated within the U-shaped channel of an implant, the Offset Mini-Corkscrew would prevent installation of a cap to secure the rod therein. Further, manipulation of the Offset Mini-corkscrew relative to the Hook/Screw Holder is time consuming and somewhat inconvenient.

There is a need for a device for seating a spinal rod in a U-shaped channel of an open ended implant which permits capping of the implant while the rod is maintained in the seated alignment.

SUMMARY OF THE INVENTION

The present invention comprises a set of tools for use in seating a spinal rod in a rod receiving channel in a head of an open ended spinal surgery implant such as a bone screw, hook or transverse connector. The set of tools according to the invention allows a surgeon to push or translate a rod toward and into the open heads of spinal implants and/or to pull or translate one or more bones with the implants thereon toward the rod so as to receive the rod in open heads of the implants. The tools are designed to permit installation of an implant cap on the head of an open ended spinal surgery implant while maintaining the spinal rod in a seated alignment therewith.

Each of the tools comprises an implant holder for grasping, holding or engaging an implant, and a pusher assembly including a pusher bar advanceable relative to the implant holder to drive, push or force a spinal rod into the rod receiving channel of an implant held by the implant holder or to draw the implant toward the rod such that the rod is received by the implant. The implant holders are of various configurations to facilitate holding or grasping of different types of implants or to accommodate different situations relating to the location of the implant. The pusher assembly is adapted for interchangeable use with each of the various implant holders.

Each of the implant holders includes a handle portion and an implant engaging portion. The implant engaging portion includes opposed engaging members for securing one of the implants therebetween. In one of the preferred embodiments, the implant holder is of unitary construction and the relative position of the engaging members is fixed. In other preferred embodiments, the implant holder is formed from two arms, each comprising a handle portion and an implant engaging portion or implant engaging member, secured together in a scissor like fashion such that the implant engaging members may be advanced between open and closed positions relative to one another.

In one aspect of the present invention, the pusher bar includes a pair of opposed legs defining a slot extending therebetween. A lower cross member extends between the opposed legs at lower ends thereof and an upper cross member extends between the opposed legs at upper ends thereof. The lower cross member or abutment member is adapted to engage a spinal rod and advance the spinal rod into a seated relationship with the rod receiving channel of an implant.

The seating apparatus utilizing the pusher assembly with the slotted pusher bar is adapted for use in combination with a cap inserter having a handle, a stem and a head, the head of the cap inserter having a socket formed therein and adapted for removably securing an implant cap to the head of the cap inserter. The slot in the pusher bar is sized to allow insertion therethrough of a cap and at least a portion of the cap inserter, to which the cap is removably secured. With the pusher bar pushing or holding a spinal rod in seated relationship in the rod receiving channel of an implant, a cap may be installed on the implant via access through the slot in the pusher bar.

In another aspect of the present invention the pusher assembly includes a threaded stem rotatably connected to the pusher bar along the upper cross member. A receptacle having a threaded bore extending therethrough is fixedly secured to the handle portion of the implant holder. The threaded stem is removably securable within the threaded bore of the receptacle for use in mechanical advancement of the pusher bar toward and away from an implant held by the implant holder by rotation of the threaded stem.

A pair of guides, which define a pair of pusher bar receiving channels may also be secured to the implant holder such that at least portions of the opposed legs of the pusher bar may be extended therethrough to guide advancement of the pusher bar relative to the implant holder.

In another aspect of the invention the implant holder includes a structural member or web having a lower edge extending transverse to the axis of the rod receiving channel of an implant secured between the implant engaging members. An opening extends between the lower edge of the web and the head of an implant secured between the implant engaging members. The lower edge of the web is adapted to function as a fulcrum for the stem of a cap inserter which must be advanced through an arcuate motion to install a cap on an implant. The distance that the lower edge of the web is spaced from an implant secured between the implant engaging members is preferably selected to facilitate installation of a cap utilizing the cap inserter.

OBJECTS AND ADVANTAGES OF THE INVENTION

The objects and advantages of the invention include: to provide a set of tools for use in seating a spinal rod in a rod receiving channel in a head of an open ended spinal surgery implant such as a bone screw, hook or transverse connector by relative translation of the rod and implant toward one another; to provide such a set of tools which facilitates the installation of a cap onto the open ended spinal surgery implant while maintaining the spinal rod seated relative thereto; to provide such a set of tools comprising multiple tools each adapted for a different use; to provide such a set of tools with different tools for use with different implants; to provide such a set of tools wherein each tool comprises an implant holder for grasping holding or engaging an implant, and a pusher assembly to drive or force a spinal rod into the rod receiving channel of an implant held by the implant holder; to provide such a set of tools in which the pusher assembly is adapted for interchangeable use with different implant holders; to provide such a set of tools in which the pusher assembly is securable to the implant holders; to provide such a set of tools which is adapted for use with tools for use in installing caps having sets screws with break off heads secured thereto; and to provide such a set of tools which are relatively easy to use and particularly well adapted for their intended usage.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a front plan view of a spinal rod pusher assembly of a spinal rod seating apparatus of the present invention.

FIG. 2 is an enlarged and fragmentary view of the pusher assembly as shown in FIG. 1 with portions broken away to show interior detail.

FIG. 3 is a cross-sectional view taken along line 3—3 of FIG. 2.

FIG. 4 is a front plan view of an implant holder of the spinal rod seating apparatus of the present invention.

FIG. 5 is an enlarged bottom plan view of the implant holder as shown in FIG. 4 taken generally along line 5—5 of FIG. 4.

FIG. 6 is an enlarged and fragmentary rear plan view of the implant holder taken generally along line 6—6 of FIG. 5.

FIG. 7 is a front plan view of the spinal rod seating apparatus of the present invention showing the pusher assembly secured to the implant holder.

FIG. 8 is an enlarged and fragmentary view of the spinal rod seating apparatus as shown in FIG. 7 and showing the spinal rod seating apparatus positioned to drive a spinal rod into a seated alignment with an open ended bone screw.

FIG. 9 shows a view similar to FIG. 8 in which a spinal rod has been driven into a seated alignment with an open ended bone screw by the spinal rod seating apparatus.

FIG. 10 is a fragmentary front plan view of a saddle cap inserter for use in association with the spinal rod seating apparatus and with portions broken away to show interior detail.

FIG. 11 is an exploded and fragmentary perspective view showing a saddle cap inserter positioned for installing a saddle cap with a set screw secured thereto, onto the head of an open ended bone screw with a spinal rod extending therebetween.

FIG. 12 is a fragmentary, right side elevational view of the spinal rod seating apparatus as shown in FIG. 9 with a spinal rod seated in the head of an open ended bone screw and with portions broken away to show the positioning of a saddle cap inserter relative to the seating apparatus for installing the cap on the bone screw with a spinal rod extending therebetween.

FIG. 13 is a fragmentary rear plan view of the spinal rod seating apparatus as shown in FIG. 12 in which the cap inserter has been used to install the cap.

5

FIG. 14 is a fragmentary and reduced right side elevational view of the spinal rod seating apparatus as shown in FIG. 12 with a saddle cap inserter positioned for installing a cap on a bone screw.

Figures 15, 16, 17, 18, 19:
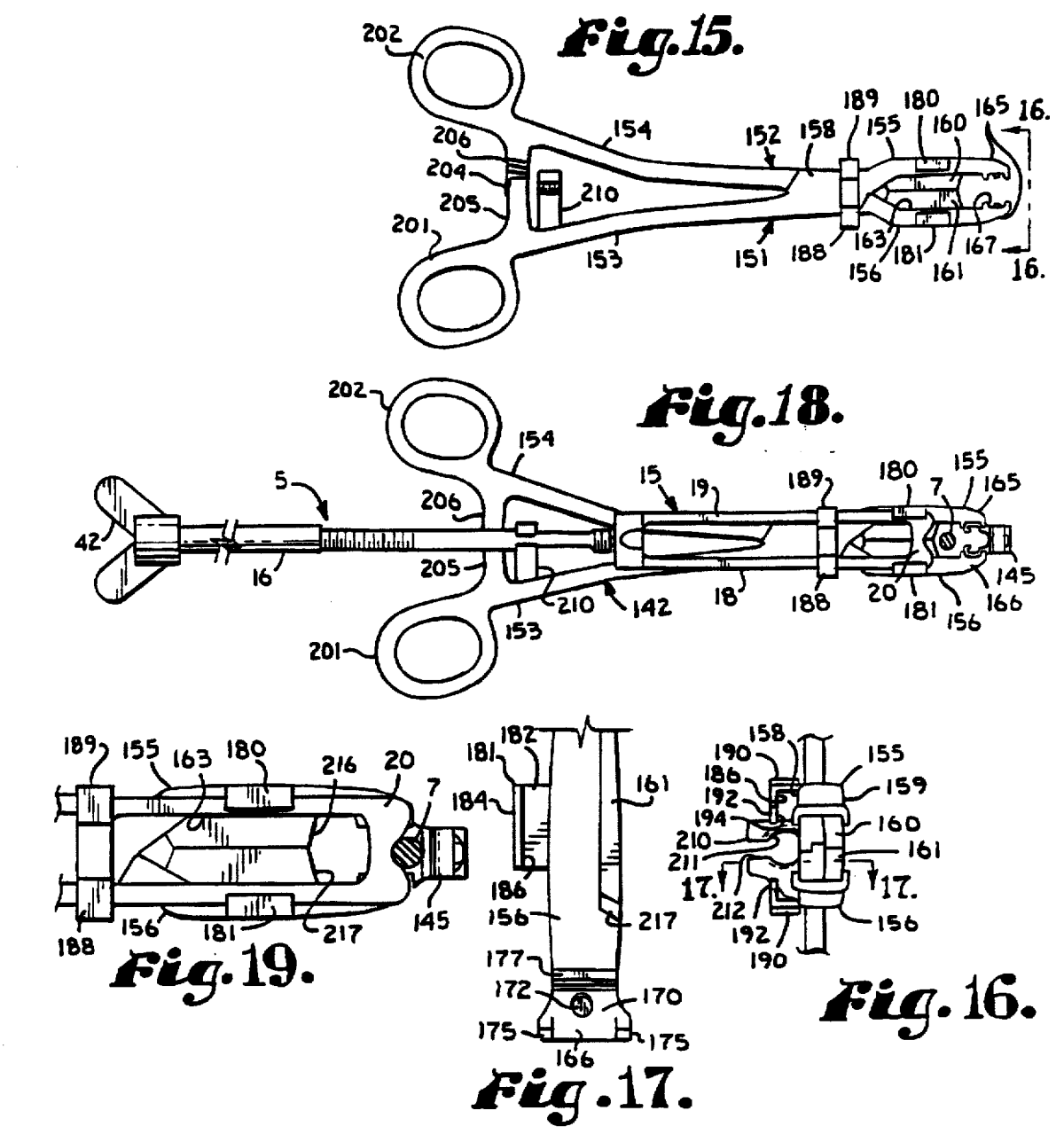

FIG. 15 is a front plan view of an implant holder of an alternative embodiment the present invention.

FIG. 16 is an enlarged and fragmentary end plan view of the implant holder as shown in FIG. 15.

FIG. 17 is an enlarged and fragmentary cross-sectional view taken generally along line 17—17 of FIG. 16.

FIG. 18 is a front plan view of the alternative embodiment showing the spinal rod engaging assembly secured to the implant holder shown in FIG. 15 and with the spinal rod engaging assembly positioned for advancing a spinal rod into a seated alignment in the head of an open ended hook.

FIG. 19 is an enlarged and fragmentary view of the spinal rod seating apparatus as shown in FIG. 18 showing the spinal rod advanced into seated alignment with the hook.

FIG. 20 is a front plan view of an open ended hook.

FIG. 21 is a left side elevational view of the open ended hook.

FIG. 22 is a fragmentary front plan view of the spinal rod seating apparatus as shown in FIG. 19 showing a saddle cap inserter positioned relative to the spinal rod seating apparatus for seating a saddle cap in a hook held thereby.

FIG. 23 is an enlarged and fragmentary right side elevational view of the spinal rod seating apparatus as generally shown in FIG. 22 with portions broken away to show the relative positioning of a saddle cap inserter to the seating apparatus for installing a cap on the head of a hook held thereby.

FIG. 24 is a front plan view of an implant holder of a second alternative embodiment of the spinal rod seating apparatus of the present invention.

FIG. 25 is an enlarged and fragmentary right side elevational view of the implant holder as shown in FIG. 24.

FIG. 26 is a cross-sectional view taken along line 26—26 of FIG. 25.

FIG. 27 is a fragmentary cross-sectional view taken along line 27—27 of FIG. 25.

FIG. 28 is an enlarged and fragmentary right side elevational view of the implant holder as shown in FIG. 24 with a spinal rod pusher assembly secured thereto and with the seating apparatus positioned to drive a spinal rod into a rod receiving groove in the head of an open ended bone screw held by the implant.

FIG. 29 is a view similar to FIG. 28 showing the spinal rod positioned in a seated alignment relative to the bone screw held by the implant holder.

FIG. 30 is a fragmentary and enlarged top plan view taken generally along line 30—30 of FIG. 24.

FIG. 31 is a front plan view of the second embodiment of the spinal rod seating apparatus as generally shown in FIG. 29 holding a spinal rod in seated alignment with an open ended bone screw and showing a saddle cap inserter positioned relative to the spinal rod seating apparatus for inserting a saddle cap in the head of a bone screw held by the spinal rod seating apparatus.

FIG. 32 is an enlarged and fragmentary front plan view of the second embodiment of the spinal rod seating apparatus similar to FIG. 31 and with portions broken away to show detail and with the saddle cap inserter having been used to install a saddle cap in a bone screw held by the spinal rod seating apparatus.

6

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, and in particular FIGS. 1–9, the reference numeral 1 refers to one embodiment of a spinal rod seating apparatus or spinal rod jack of the present invention which is shown fully assembled in FIG. 7. The apparatus 1 comprises a spinal rod pusher assembly 5, as shown in FIGS. 1–3, and an implant holder 6, as shown in FIGS. 4–6.

The apparatus 1 is particularly adapted for seating a spinal rod 7 in a rod receiving channel 8 in a head 9 of an open ended implant 10 such as the bone screw 11 shown in FIGS. 8 and 9. The apparatus 1 is further adapted to facilitate the installation of a cap 12 on the open ended implant 10 while the spinal rod 7 is seated in the rod receiving channel 8 therein as generally shown in FIGS. 11 through 13.

The spinal rod pusher assembly 5 comprises a pusher bar or rod engaging member 15 and a stem 16. The pusher bar 15 is generally elongate and includes a pair of opposed legs 18 and 19 maintained in spaced apart relation by an abutment member 20, extending between the legs 18 and 19 at a distal end thereof, and a connector strut or member 22 extending between the legs 18 and 19 at an opposite end thereof. An elongate slot or opening 23 is formed between the legs 18 and 19 and the abutment member 20 and the connector member 22.

A semi-circular rod receiving indent or cutout 24 is formed on an outer edge or surface of the abutment member 20 and is sized and shaped to conform to the shape of a portion of the outer surface of a spinal rod 7. A relief 25 is formed on a front face 26 of the connector strut 22.

The stem 16 is rotatably connected to the connector member 22. In particular and as shown in FIGS. 2 and 3, a cylindrical shaft 30 extends in axial alignment away from a first end 31 of the stem 16. A peripheral groove 32 is formed in the cylindrical shaft 30. The shaft 30 is rotatably positioned in a cylindrical bore 33 in the connector strut 22. A set screw 34 extends through a set screw receiving bore 35 in the connector strut 22 and into the peripheral groove 31 in the cylindrical shaft 30 to secure the stem 16 to the connector strut 22 while permitting rotation of the stem 16 relative to the strut 22.

A substantial portion of the stem 16 is threaded on an outer surface thereof and may be referred to as a threaded portion 40. The threaded portion extends from the first end 31 of the stem 16 toward a second end 41 thereof. Grasping means such as wings 42 are secured to the second end 41 of the stem 16 to facilitate manual rotation of the stem 16 relative to the pusher bar 15.

Cutouts 43 and 44 are formed on opposite sides of the threaded portion of the stem 16 toward the first end 31 thereof such that the portion of the stem 16 adjacent the cutouts 43 and 44 is generally flattened and may be referred to as a flattened portion 46.

The implant holder or jack base 6 generally comprises a handle portion 51 and an implant engaging portion 52 and has a front face 54 and a rear face 55. The handle portion 51 of the implant holder 6 includes a rear wall 56 and sidewalls 57 and 58 extending forwardly from the rear wall 56 on opposite sides thereof. A groove or channel 59 extends between or is defined by the sidewalls 57 and 58.

Implant engaging members 60 and 61 generally comprise extensions of sidewalls 57 and 58 respectively and extend past a lower end 62 of the handle 51 on opposite sides thereof to form a slot 63 extending therebetween. Distal ends 65 and 66 of the implant engaging members 60 and 61 respectively curve or extend inward and generally form a cradle or socket 67.

Abutment shoulders 70 and 71 extend partially into the slot 63 from the implant engaging members 60 and 61 respectively along the distal ends 65 and 66 thereof. The abutment shoulders 70 and 71 extend from a front face 72 of each of the implant engaging members 60 and 61 respectively. A web 75, having a front lower edge 76, extends between the implant engaging members 60 and 61 generally across the rear face 55 of the implant holder 6.

Guides 80 and 81 are secured to the implant engaging members 60 and 61 respectively. The guides 80 and 81 generally comprise inwardly facing L-shaped shoulders each having a support leg 82, extending away from the front face 54 of the holder 6, and an abutment leg 84, extending parallel to the front face 54 of the holder 6 and defining a channel 86.

A receptacle 90 is formed on the handle portion 51 at a distal end 91 thereof. The receptacle 90 extends forward from and transverse to the rear wall 56 of the handle portion 51. A threaded bore 92 extends through the receptacle 90. The axis of the threaded bore 92 extends in parallel alignment with the axis of the implant holder 6. An access slot 93 extends through the receptacle 90 and into communication with the threaded bore 92. The slot 93 extends into the receptacle 90 generally along a front face 54 of the implant holder 6. The access slot 93 is slightly wider than the width of the flattened portion 46 of the stem 16 but narrower than the diameter of the stem 16.

The spinal rod pusher assembly 5 is secured to the implant holder 5 by advancing or dropping the flattened portion 46 of the stem 16 through the access slot 93 and into the threaded bore 92 such that the pusher bar 15 is generally positioned against the front face 54 of the implant holder 6 between the receptacle 90 and the guides 80 and 81. The stem 16 is then rotated to threadingly advance the stem 16 relative to the receptacle 90 and advance the pusher bar 15 toward the implant engaging portion 52 of the implant holder 6. The pusher bar 15 is advanced toward and away from the implant engaging portion 52 of the implant holder 6 through rotation of the stem 16.

To prepare the apparatus 1 for use, the pusher bar 15 is advanced such that at least the outer portions of the opposed legs 18 and 19 pass through the channels 86 formed by the guides 80 and 81 respectively, and a leading edge of the abutment member 20 of the pusher bar 15 is advanced slightly past a lower end 76 of the web 75 of the implant holder 6.

To use the apparatus 1 to seat a spinal rod 7 in the rod receiving channel 8 of a bone screw 11 secured to a vertebra, the apparatus 1 is positioned such that the implant engaging members 60 and 61 straddle the spinal rod 7 and the rear face 55 of the implant engaging portion 52 is generally aligned with and directed toward a face of the bone screw 11. The implant engaging portion 52 of the holder 6 is then advanced across or over the head 9 of the screw 11 until the abutment shoulders 70 and 71 abut against and engage outer portions of the screw head 9 such that the implant engaging members 60 and 61 envelope or are positioned adjacent to the sides of the screw head 9 and the screw head 9 is generally positioned in the cradle or socket 67 of the implant holder 6 as shown in FIG. 8. The inwardly curved distal ends 65 and 66 of the implant engaging members 60 and 61 respectively abut against the outwardly diverging lower surfaces of the bone screw head 9 and prevent the implant holder from being pulled axially away from the screw 11.

The surgeon (not shown) then rotates the stem 16 to advance the pusher bar 15 toward the bone screw 11 positioned within the cradle 67 of the implant engaging portion 52 until the abutment member 20 of the pusher bar 15 engages the spinal rod 7 such that a portion of the rod 7 extends into the rod receiving indent 24. As the surgeon continues to threadingly advance the pusher bar 15, the spinal rod 7 and the bone screw head 9 are drawn together such that the spinal rod 7 is seated in the rod receiving channel 8 of the bone screw head 9.

FIGS. 10 and 11 show a cap inserter or saddle cap inserter 100 which is adapted for use in inserting a cap, saddle or saddle cap 12 into an open end type implant 10, such as the bone screw 11. The rod receiving channel 8 of the bone screw 11 is generally U-shaped and is formed in the head 9 between opposed channel sidewalls 102 and 103. A curved slot 104 and 105 is formed in each sidewall 102 and 103 respectively on inner opposed faces thereof.

The saddle cap 12 includes a central portion 106 and outwardly extending curved flanges or tongues 107 and 108 formed on opposite sides thereof. A downwardly opening rod conforming channel 109 is formed on the bottom of the cap central portion 106. A set screw receiving bore 110 extends through the central portion 106 from an upper end thereof to the rod conforming channel 109.

The saddle cap 12 includes a front face 112 and a rear face 113. Leading edges 114 of the tongues 107 and 108 adjacent the cap front face 112 are slightly curved.

After a rod 7 is inserted into or seated in the U-shaped channel 8 of the bone screw 11 a saddle cap 12 may be attached to the head 9 of the bone screw 10 to secure the rod 7 therein. A set screw 120, having a head 121 and a threaded portion 122, and which is positioned in the set screw receiving bore 110 in the cap 12 is then tightened to fix the position of the rod 7 relative to the bone screw 11. A cylindrical bore 123 extends into the set screw head 121 axially therewith. The set screw 120 is tightened until a preselected torque is exceeded and the head 121 breaks off.

The saddle cap 12 is attached to the head 11 of the bone screw 11 by positioning the saddle cap 12 adjacent the bone screw 11, at a slightly downward angle, such that the leading edges 114 of the tongues 107 and 108 are aligned with one end of the curved slots 105 and 106. The saddle cap 12 is then advanced forward and rotated upward such that the tongues 107 and 108 extend into the curved slots 105 and 106 respectively.

The saddle cap 12 is preferably wedge shaped in that the distance across the rear face 113 of the saddle cap 12 is slightly greater than the distance across the front face 112 of the saddle cap 12. In addition, the distance across the front face 112 of the saddle cap 12 is slightly smaller than the distance between the sidewalls 102 and 103 while the distance across the rear face 113 of the saddle cap 12 is slightly greater than the distance between the sidewalls 102 and 103. The wedge shape of the saddle cap 12 forms an interference fit between the saddle cap 12 and the sidewalls 102 and 103 when inserted therebetween.

The cap inserter 100 includes a tool body 124 having a handle 125, a stem 126, and a head 127 which has a socket 128 formed therein. An insert receiving bore 129, extends through the tool body 124 and in communication with the socket 124.

The handle 125 is preferably cylindrical with a knurled outer surface to facilitate gripping. The stem 126 extends in axial alignment with the handle 125 from a lower end thereof.

A tab or abutment member 130 depends from a lower end of the head 127 of the tool body 124 on one side thereof. The abutment member 130 is adapted for positioning in abutting relationship against the rear face 113 of a saddle cap 12.

The socket 128 of the tool body 124 is generally cylindrical and slightly larger in diameter than the diameter of the set screw head 121 such that the head 121 of a set screw 120 may be freely rotated within the socket 128.

The saddle cap inserter 100 also comprises a set screw engaging insert 134. The set screw engaging insert 134 comprises a shaft 135 having a cap 136 secured at one end and a nipple or projection 137 extending axially away from an opposite end thereof. The shaft 135 is cylindrical and sized for insertion into and through the insert receiving bore 129 in the tool body 124.

The saddle cap inserter 100 is particularly adapted for use in inserting saddle caps 12 having set screws 120 preloaded in the set screw receiving bores 110 of the saddle caps 12. With the set screw engaging insert 134 inserted into the handle 125 and stem 126, such that the projection 137 extends into the socket 128, the head 121 of a set screw 120 secured to a cap 12 can be inserted into the socket 128 such that the projection 137 extends into the bore 123 in the set screw 120 and such that the abutment member 130 extends in abutting relationship with the rear face 113 of the saddle cap 12. Biasing means, such as a split washer type spring 1 secured within a peripheral groove (not shown) in the projection 137 biasingly engages an internal wall of the set screw 120 and thereby grips or holds the set screw 120 onto the projection 137 and in turn grips or holds the saddle cap 12, to which the set screw 120 is attached, to the cap inserter 100. Abutment of the abutment member 130 against the rear face 113 of the saddle cap 12 prevents the saddle cap 12 from rotating relative to the set screw 120 during manipulation and insertion of the saddle cap 12 and thereby facilitates insertion.

With the saddle cap 12 secured to the saddle cap inserter 100, the saddle cap inserter 100 can then be used to insert the saddle cap 12 into an open ended type implant 10 such as a bone screw 11 as previously discussed.

The spinal rod seating apparatus 1 is particularly adapted to facilitate use of a tool such as the saddle cap inserter 100 for installing a saddle cap 12 in the head 9 of an open ended implant 10 such as bone screw 11, while the pusher bar 15 holds the spinal rod 7 in a seated alignment with the bone screw head 9 as generally shown in FIGS. 12 through 14.

The lower portion of the saddle cap inserter 100, with a saddle cap 12 secured thereto, is directed or advanced through the elongate slot 23 between the opposed legs 18 and 19 of the pusher bar 15, generally horizontally or angled slightly downward, and into the slot 63, until the saddle cap is advanced slightly past the bone screw head 9. The saddle cap 12 is aligned with or positioned with respect to the bone screw head 9 such that the leading edges 114 of the tongues 107 and 108 are aligned with the ends of the curved slots 105 and 106 on the side of the screw head 9 opposite the pusher bar 15.

The handle 125 of the saddle cap inserter 100 is then rotated upward toward the handle portion 51 of the implant holder 6. As the handle 125 is rotated upward, a lower portion of the stem 126 of the saddle cap inserter tool body 124 engages the front lower edge 76 of the web 75 which generally functions as a fulcrum. As the handle 125 is further rotated upward, the saddle cap inserter 100 pivots about the front lower edge 76 of the web 75 and the saddle cap 12 is advanced forwardly and along an arc such that the tongues 107 and 108 extend into the curved slots 105 and 106 respectively.

The length of the elongate slot 23 allows the saddle cap inserter 100 to be rotated or pivoted through an arc of up to approximately eighty degrees from horizontal which provides for sufficient insertion of the saddle cap 12 within the screw head 9 for purposes of fixing the relative relationship of the spinal rod 7 within the rod receiving channel 8. The relief 25 in the connector member 22 is also intended to facilitate advancement of the saddle cap inserter 100 to as close to vertical alignment with the spinal rod seating apparatus 1 as possible.

The distance between the head 9 of a bone screw 11 secured in the implant holder 6 to the front lower edge 76 of the web 75 is selected to facilitate insertion of caps 12 into the bone screw head 9. In particular, the distance between the bone screw head 9 and the front lower edge 76 of the web 75 is selected such that the radius of the arc of rotation of the tongues 107 and 108 of a cap 12 secured to the inserter 100 as the inserter is pivoted about the web front lower edge 76 corresponds to the radius of the curved slots 104 and 105 in the bone screw head 9.

After the saddle cap 12 is at least partially inserted in the bone screw head 9 as discussed above, the inserter 100 and then the spinal rod seating apparatus can be removed. The inserter 100 can then be reattached to the saddle cap 12 to finalize insertion of the cap 12 in the bone screw head 9. After the cap is inserted, the set screw 120 can be tightened down to fix the position of the rod 7 to the bone screw head 9 and to the point necessary to shear off the set screw head 121.

Referring to FIGS. 15 through 19, the reference numeral 141 refers to an alternative embodiment of the spinal rod seating apparatus of the present invention, shown fully assembled in FIG. 18 and which includes a hook holder 142 and a spinal rod pusher assembly 5 which is identical to and interchangeable with the spinal rod pusher assembly 5 as discussed with respect to the spinal rod seating apparatus 1. The spinal rod seating apparatus 141 is particularly adapted for inserting spinal rods 7 within a rod receiving channel 143 in the head 144 of an open ended spinal surgery implant 10 such as an open ended hook 145 as shown in FIGS. 20 and 21. The head 144 of the open ended hook 145 includes opposed sidewalls 146 and 147 each having a curved slot 148 and 149 formed on inner opposed faces thereof. A post receiving bore 150 extends through each of the sidewalls 146 and 147 of the hook head 144.

The hook holder 142 generally comprises a modified clamping type forceps having a first arm 151 and a second arm 152 pivotally secured together in a scissor like fashion. Each arm 151 and 152 comprises a handle portion 153 and 154 respectively and an implant engaging portion or member 155 and 156 respectively. The hook holder 142 includes a front face 158 and a rear face 159.

Web portions 160 and 161 are secured to and extend inward from implant engaging members 155 and 156 respectively generally along a rear face 159 thereof. When the implant engaging members 155 and 156 are advanced to a closed relationship the web portions 160 and 161 are advanced in abutting relationship to form a single web. When the implant engaging members 155 and 156 are advanced to a closed relationship a slot 163 generally extends therebetween.

Distal ends 165 and 166 of the implant engaging members 155 and 156 respectively extend slightly inward and generally form a cradle or socket 167 when the implant engaging members 155 and 156 are advanced to a closed alignment. The distal ends 165 and 166 of the implant engaging members 155 and 156 each include an inwardly facing implant engaging surface 170 with a cylindrical post 172 extending inward therefrom as shown in FIG. 17. The implant engaging surfaces 170 are shaped to conform to the shape of hook head sidewalls 146 and 147. Fingers or abutments 175 extend inward from each of the implant engaging surfaces 170 along a lower edge thereof and on opposite sides thereof. A shoulder or ridge 177 extends across each of the implant engaging surfaces 170 along an upper edge thereof.

When the implant engaging members 155 and 156 are advanced to a closed position, the normal distance between the implant engaging surfaces 170 is slightly smaller than the distance between the outer surfaces of the hook sidewalls 146 and 147 such that the implant engaging surfaces 170 biasingly engage the head 144 of a hook 145 positioned therebetween.

For securing the hook 145 between the implant engaging members 155 and 156, the implant engaging members 155 are positioned in encompassing relationship with the hook head 144 such that when the implant engaging members 155 and 156 are advanced to a closed position, the sidewalls 146 and 147 are generally positioned between the fingers 75 and ridge 77 on the respective implant engaging member 155 and 156 and the cylindrical post 172 on the members 155 and 156 extends into the post receiving bore 150 of the respective hook sidewall 146 and 147. In such an arrangement, the hook head 144 may generally be described as being positioned or secured within the socket 167 of the hook holder 142.

Lower guides 180 and 181 are secured to the implant engaging members 155 and 156 respectively. The guides 180 and 181 generally comprise inwardly facing L-shaped shoulders each having a support leg 182, extending away from the front face 158 of the hook holder 142, and an abutment leg 184, extending parallel to the front face 158 of the holder 142 and defining a channel 186.

Secondary guides 188 and 189 are secured to the first arm 151 of the hook holder 142 on a front face 158 thereof. The secondary guides 188 and 189 generally comprise inwardly facing L-shaped shoulders each having a support leg 190, extending away from the front face 158 of first arm 151 the hook holder 142, and an abutment leg 192, extending parallel to the front face 158 and defining a channel 194. The channels 194 of the secondary guides 188 and 189 are axially aligned with the respective channels 186 of the lower guides 180 and 181.

Finger rings 201 and 202 are mounted on the distal ends of the handle portions 153 and 154. A conventional clamping assembly 204 such as first and second saw toothed clamping members 205 and 206 are mounted on the first and second handle portions 153 and 154 respectively proximate the distal ends thereof. The clamping assembly 204 may be utilized to lock or hold the implant engaging members 155 and 156 in the closed position.

A receptacle 210 is formed on the first handle portion 153 proximate a distal end thereof. The receptacle 210 extends forward from and transverse to the front face 158 of the hook holder 142. A threaded bore 211 extends through the receptacle 210. The axis of the threaded bore 211 extends in parallel alignment with the axis of the hook holder 142 in the closed position. An access slot 212 extends through the receptacle 210 and into communication with the threaded bore 211. The slot 212 extends into the receptacle 210 generally along a front face 258 of the hook holder 142. The access slot 212 is slightly wider than the width of the flattened portion 46 of the stem 16 of the spinal rod pusher assembly 5, but narrower than the diameter of the stem 16.

The spinal rod pusher assembly 5 is secured to the hook holder 142 by advancing or dropping the flattened portion 46 of the stem 16 through the access slot 212 and into the threaded bore 211 such that the pusher bar 15 is generally positioned against the front face 158 of the hook holder 142 between the receptacle 210 and the secondary guides 188 and 189. The stem 16 is then rotated to threadingly advance the stem 16 relative to the receptacle 210 and advance the pusher bar 15 through the channels 194 of the guides 188 and 189 and through the channels 186 of the lower guides 180 and 181 and socket 167 of the hook holder 142. The pusher bar 15 is advanced toward and away from the implant engaging members 155 and 156 of the hook holder 142 through rotation of the stem 16.

To prepare the spinal rod seating apparatus 141 for use, the pusher bar 15 is advanced such that at least the outer portions of the opposed legs 18 and 19 pass through the channels 194 formed by the secondary guides 188 and 189 and through the channels 186 formed by the lower guides 180 and 181 respectively, and a leading edge of the abutment member 20 of the pusher bar 15 is advanced slightly past a lower end of the webs 160 and 161 of the hook holder 142.

To use the apparatus 1 to seat a spinal rod 7 in the rod receiving channel 143 of a hook 145 secured or connected to an osteosynthesis assembly (not shown) the apparatus 141 is positioned such that the implant engaging members 155 and 156 straddle the spinal rod 7 and the distal ends 165 and 166 of the implant engaging members 155 and 156 are generally positioned in encompassing relationship with the hook head 144 as discussed above. The implant engaging members 155 and 156 are then advanced to the closed position to secure the hook head 144 therebetween in the socket 167 as discussed previously. The inwardly curved distal ends 165 and 166 of the implant engaging members 155 and 156 respectively abut against the outwardly diverging lower surfaces of the hook head 144 and prevent the hook holder 142 from being pulled axially away from the hook 145. Similarly, extension of the cylindrical posts 172 into the post receiving bores 150 in the sidewalls 146 and 147 of the hook head 144 prevents the hook holder 142 from being pulled axially away from the hook 145.

The surgeon (not shown) then rotates the stem 16 to advance the pusher bar 15 toward the hook 145 positioned within the cradle 167 until the abutment member 20 of the pusher bar 15 engages the spinal rod 7 such that a portion of the rod 7 extends into the rod receiving indent 24. As the surgeon continues to threadingly advance the pusher bar 15, the spinal rod 7 and the hook head 144 are drawn together such that the spinal rod 7 is seated in the rod receiving channel 143 of the hook head 144.

After a rod 7 is inserted into or seated in the U-shaped channel 143 of the hook 145, a saddle cap 12 may be attached to the hook 145 to secure the rod 7 therein. A set screw 120 which is positioned in the set screw receiving bore 110 in the cap 12 is then tightened to fix the position of the rod 7 relative to the hook 145. The set screw 120 is tightened until a preselected torque is exceeded and the head 121 breaks off.

The saddle cap 12 is attached to the head 144 of the hook 145 by positioning the saddle cap 12 adjacent the hook 145, at a slightly downward angle, such that the leading edges 114 of the tongues 107 and 108 are aligned with one end of the curved slots 148 and 149. As shown in FIG. 23, the saddle cap 12 is then advanced forward and rotated upward such that the tongues 107 and 108 extend into the curved slots 148 and 149 respectively.

With the saddle cap 12 secured to the saddle cap inserter 100, the saddle cap inserter 100 can then be used to insert the saddle cap 12 into an open ended type implant 10 such as a hook head as previously discussed.

The spinal rod seating apparatus 141 is particularly adapted to facilitate use of a tool such as the saddle cap inserter 100 for installing a saddle cap 12 in the head 144 of an open ended hook 145, while the pusher bar 15 holds the spinal rod 7 in a seated alignment with the hook head 144 as generally shown in FIGS. 22 and 23.

The lower portion of the saddle cap inserter 100, with a saddle cap 12 secured thereto, is directed or advanced through the elongate slot 23 between the opposed legs 18 and 19 of the pusher bar 15, generally horizontally or angled slightly downward, and into the slot 163 in the hook holder 142 until the saddle cap is advanced slightly past the hook head 144. The saddle cap 12 is aligned with or positioned with respect to the hook head 144 such that the leading edges 114 of the tongues 107 and 108 are aligned with the ends of the curved slots 148 and 149 on the side of the hook head 144 opposite the pusher bar 15.

The handle 125 of the saddle cap inserter 100 is then rotated upward toward the handle portions 153 and 154 of the hook holder 142. As the handle 125 is rotated upward, a lower portion of the stem 126 of the saddle cap inserter tool body 124 engage front lower edges 216 and 217 respectively of the webs 160 and 161 which generally function as a fulcrum. As the handle 125 is further rotated upward, the saddle cap inserter 100 pivots about the front lower edges 216 and 217 of the webs 160 and 161 and the saddle cap 12 is advanced forwardly and along an arc such that the tongues 107 and 108 extend into the curved slots 148 and 149 respectively.

The length of the elongate slot 23 allows the saddle cap inserter 100 to be rotated or pivoted through an arc of up to approximately eighty degrees from horizontal which provides for sufficient insertion of the saddle cap 12 within the hook head 144 for purposes of fixing the relative relationship of the spinal rod 7 within the rod receiving channel 143. The relief 25 in the connector member 22 is also intended to facilitate advancement of the saddle cap inserter 100 to as close to vertical alignment with the spinal rod seating apparatus 141 as possible.

The distance between the head 144 of a hook 145 secured in the hook holder 142 to the front lower edges 216 and 217 of the webs 160 and 161 is selected to facilitate insertion of caps 12 into the hook head 144. In particular, the distance between the hook head 144 and the front lower edges 216 and 217 of the webs 160 and 161 is selected such that the radius of the arc of rotation of the tongues 107 and 108 of a cap 12 secured to the inserter 100 as the inserter is pivoted about the web front lower edges 216 and 217 corresponds to the radius of the curved slots 148 and 149 in the hook head 144.

After the saddle cap 12 is at least partially inserted in the hook head 144 as discussed above, the inserter 100 and then the spinal rod seating apparatus 141 can be removed. The inserter 100 can then be reattached to the saddle cap 12 to finalize insertion of the cap 12 in the hook head 144. After the cap is inserted, the set screw 120 can be tightened down to fix the position of the rod 7 to the hook head 144 and to the point necessary to shear off the set screw head 121.

Referring to FIGS. 24 through 32, the reference numeral 225 refers to an alternative embodiment of the spinal rod seating apparatus of the present invention, shown fully assembled in FIG. 30 and which includes an implant holder 226, as shown in FIGS. 24 through 26 and a spinal rod pusher assembly 5 which is identical to and interchangeable with the spinal rod pusher assembly 5 as discussed with respect to the spinal rod seating apparatus 1. The spinal rod seating apparatus 225 is particularly adapted for inserting spinal rods 7 within a rod receiving channel 8 in the head 9 of an open ended spinal surgery implant 10 such as a bone screw 11 when access to at least one of the sidewalls 102 and 103 is obstructed.

The implant holder 225 generally comprises a modified clamping type forceps having a first arm 227 and a second arm 228 pivotally secured together in a scissor like fashion. Each arm 227 and 228 comprises a handle portion 229 and 230 respectively and an implant engaging portion or member 231 and 232 respectively. The implant holder 225 includes a front face 233 and a rear face 234.

Distal ends 237 and 238 of the implant engaging members 231 and 232 respectively extend forwardly from the front face 233 of the holder 226. Inwardly facing recesses 240 and 241 are formed in the distal ends 237 and 238 of the implant engaging members 230 and 231 such that when the implant engaging members are advanced to a closed position, the recesses form a cradle or socket 243 adapted to engage and secure the head 9 of a bone screw 11, or other implant therein. In particular, the inwardly facing recesses 240 and 241 are defined by inwardly facing implant engaging surfaces 245 and 246 which generally extend across the front and rear faces respectively of the bone screw head 9 and below the sidewalls 102 and 103 thereof when the implant engaging members 230 and 231 are advanced to a closed position.

When the implant engaging members 230 and 231 are advanced to a closed position, the distance between the implant engaging surfaces 245 and 246 is slightly smaller than the distance between the front and rear face of the bone screw head 9 such that the implant engaging surfaces 245 and 246 biasingly engage the head 9 of a bone screw 11 positioned therebetween.

Semicircular depressions 248 and 249 are formed in the distal ends 237 and 238 of the implant engaging members 231 and 232 respectively and are sized and shaped to receive portions of a spinal rod 7 extending beyond the rod receiving channel 8 of a bone screw 11 secured between the implant engaging members 231 and 232.

When a bone screw 11 is secured within the socket 243, the axis of the rod receiving channel 8 generally extends parallel to the front face 232 of the implant holder 226.

A pusher bar support member 255 is secured to the first arm 227 of the implant holder 226 on a front face 233 thereof and extends forward therefrom. The support member 255 includes a left support surface 256 and a right support surface 257. The left and right support surfaces 256 and 257 angle slightly outward from top to bottom relative to a vertical axis of the implant holder 226.

A left side outer guide 260 and a left side inner guide 261 are secured to the pusher bar support member 255 on opposite sides of the left support surface 256. The left side outer guide 260 generally comprises an inwardly facing L-shaped shoulder having a support leg 262, extending away from the left support surface 256, and an abutment leg 263, extending parallel to and over the left support surface 256 and defining a channel 264. The left side inner guide 261 generally comprises an inwardly facing L-shaped shoulder formed by an abutment leg 267 extending forwardly from the first arm 227 of the implant holder 226 in spaced relation to the left support surface 256 to define a channel 268 which is aligned with channel 264.

A right side outer guide 270 and right side inner guide 271 are secured to the pusher bar support member 255 on opposite sides of the right support surface 257. The right side outer guide 270 generally comprises an inwardly facing L-shaped shoulders having a support leg 272, extending away from the right support surface 256, and an abutment leg 273 (not shown), extending parallel to and over the right support surface 256 and defining a channel 274 (not shown). The right side inner guide 271 generally comprises an inwardly facing L-shaped shoulder formed by an abutment leg 277 extending forwardly from the first arm 227 of the implant holder 226 in spaced relation to the right support surface 256 to define a channel 278 which is aligned with channel 274.

Reliefs 280 and 281 are formed in the support member 255 on the left and right support surfaces 256 and 257 respectively. The reliefs 280 and 281 generally extend upward from lower edges 282 and 283 of the left and right support surfaces 256 and 257. The support member 255 may also generally be referred to as a web.

Finger rings 286 and 287 are mounted on the distal ends of the handle portions 229 and 230. A conventional clamping assembly 288 such as first and second saw toothed clamping members 289 and 290 are mounted on the first and second handle portions 229 and 230 respectively proximate the distal ends thereof. The clamping assembly 288 may be utilized to lock or hold the implant engaging members 231 and 232 in the closed position.

A receptacle 292 is secured to the first handle portion 229 proximate a distal end thereof. The receptacle 292 extends forward from and transverse to the front face 233 of the implant holder 226. A threaded bore 293 extends through the receptacle 292. The axis of the threaded bore 293 generally extends in parallel alignment with the axis of the implant holder 226 in the closed position. The receptacle 292 is pivotally secured to the first handle portion 229 to permit at least slight pivotal rotation of the receptacle 292 such that the axis of the threaded bore 293 may be selectively aligned with the angle of the left or right support surface 256 or 257 of the support member 255. An access slot 294 extends through the receptacle 292 and into communication with the threaded bore 293. The slot 294 extends into the receptacle 292 generally along a front face 233 of the implant holder 226. The access slot 294 is slightly wider than the width of the flattened portion 46 of the stem 16 of the spinal rod pusher assembly 5, but narrower than the diameter of the stem 16.

The spinal rod pusher assembly 5 is secured to the implant holder 226 by advancing or dropping the flattened portion 46 of the stem 16 through the access slot 294 and into the threaded bore 293 and such that the pusher bar 15 is generally positioned between the receptacle 292 and the pusher bar support member 255. The stem 16 is then rotated to threadingly advance the stem 16 relative to the receptacle 292 and advance the pusher bar 15 through either the channels 264 and 268 of the left side outer and inner guides 260 and 261 respectively or the channels 274 and 278 of the right side outer and inner guides 270 and 271. The pusher bar 15 is advanced toward and away from the distal ends 237 and 238 of the implant engaging members 231 and 232 through rotation of the stem 16.

To prepare the spinal rod seating apparatus 225 for use, the pusher bar 15 is advanced such that at least the outer portions of the opposed legs 18 and 19 pass through the channels 264 and 268 or the channels 274 and 278, and a leading edge of the abutment member 20 of the pusher bar 15 is advanced slightly past the lower edge 282 or 283 of either the left or right support surface 256 or 257 respectively.

To use the apparatus 225 to seat a spinal rod 7 in the rod receiving channel 8 of a bone screw 11 secured or connected to a vertebra, the holder 226, with the arms 227 and 228 in an open alignment, is positioned such that the spinal rod 7 is generally positioned slightly below the pusher bar support member 255 and a lower end of the pusher bar 15, and the distal ends 237 and 238 of the implant engaging members 231 and 232 are generally positioned in encompassing relationship with the bone screw head 9.

The implant engaging members 231 and 232 are then advanced to the closed position to secure the bone screw head 9 therebetween in the socket 243 as discussed previously. Securement of the bone screw head 9 in the socket 243 prevents the implant holder 226 from being pulled axially away from the bone screw 11.

The surgeon (not shown) then rotates the stem 16 to advance the pusher bar 15 toward the bone screw 9 secured within the socket 243 until the abutment member 20 of the pusher bar 15 engages the spinal rod 7 such that a portion of the rod 7 extends into the rod receiving indent 24. As the surgeon continues to threadingly advance the pusher bar 15, the spinal rod 7 and the bone screw head 9 are drawn together such that the spinal rod 7 is seated in the rod receiving channel 8 of the bone screw head 9.

After a rod 7 is inserted into or seated in the U-shaped channel 8 of the bone screw 11 a saddle cap 12 may be attached to the bone screw head 9 to secure the rod 7 therein. A set screw 120 which is positioned in the set screw receiving bore 110 in the cap 12 is then tightened to fix the position of the rod 7 relative to the bone screw 11. The set screw 120 is tightened until a preselected torque is exceeded and the head 121 breaks off.

The spinal rod seating apparatus 225 is particularly adapted to facilitate use of a tool such as the saddle cap inserter 100 for installing a saddle cap 12 in the head 9 of an open ended bone screw 11, while the pusher bar 15 holds the spinal rod 7 in a seated alignment with the bone screw head 9 as generally shown in FIGS. 31 and 32.

The lower portion of the saddle cap inserter 100, with a saddle cap 12 secured thereto, is directed or advanced through the elongate slot 23 between the opposed legs 18 and 19 of the pusher bar 15, generally horizontally or angled slightly downward, and into the space between the pusher bar support member 255 and the bone screw 11 held by the implant holder 226, until the saddle cap 12 is advanced slightly past the bone screw head 9. The saddle cap 12 is aligned with or positioned with respect to the bone screw head 9 such that the leading edges 114 of the tongues 107 and 108 are aligned with the ends of the curved slots 104 and 105 on the side of the bone screw head 9 opposite the pusher bar 15.

The handle 125 of the saddle cap inserter 100 is then rotated upward toward the side of the handle portions 229 and 230 of the implant holder 226. As the handle 125 is rotated upward, a lower portion of the stem 126 of the saddle cap inserter tool body 124 engages a lower edge 282 or 283 of the pusher bar support member 255 which generally function as fulcrums. As the handle 125 is further rotated upward, the saddle cap inserter 100 pivots about the appropriate lower edge 282 or 283 of the support member 255 and the saddle cap 12 is advanced forwardly and along an arc such that the tongues 107 and 108 extend into the curved slots 104 and 105 respectively.

The length of the elongate slot 23 allows the saddle cap inserter 100 to be rotated or pivoted through an arc of up to approximately eighty degrees from horizontal which provides for sufficient insertion of the saddle cap 12 within the bone screw head 9 for purposes of fixing the relative relationship of the spinal rod 7 within the rod receiving channel 8. The reliefs 280 and 281 in the support member 255 and the relief 25 in the connector member 22 are also intended to facilitate advancement of the saddle cap inserter 100 to as close to vertical alignment with the spinal rod seating apparatus 225 as possible.

The distance between the head 9 of a bone screw 11 secured in the implant holder 226 to the lower edge 282 or 283 of the left and right support surfaces 256 or 257 is selected to facilitate insertion of caps 12 into the bone screw head 9. In particular, the distance between the bone screw head 9 and either lower edge 282 or 283 of the left or right support surface 256 or 257 respectively is selected such that the radius of the arc of rotation of the tongues 107 and 108 of a cap 12 secured to the inserter 100 as the inserter is pivoted about the appropriate lower edge 282 or 283 corresponds to the radius of the curved slots 104 and 105 in the bone screw head 9.

After the saddle cap 12 is at least partially inserted in the bone screw head 9 as discussed above, the inserter 100 and then the spinal rod seating apparatus 225 can be removed. The inserter 100 can then be reattached to the saddle cap 12 to finalize insertion of the cap 12 in the bone screw head 9. After the cap is inserted, the set screw 120 can be tightened down to fix the position of the rod 7 to the bone screw head 9 and to the point necessary to shear off the set screw head 121.

The present invention allows a surgeon to both move a rod toward bone screws and implants with attached spinal bones toward the rod. That is in some situations the rod or a portion of the rod translates toward the implants and in other situations the implants with individually or as a group are translated with attached bones toward the rod to make a correction. Simultaneous translation of rod and implants relative to the remainder of the patient is also possible.

It is to be understood that while certain forms of the present invention have been illustrated and described herein, it is not to be limited to the specific forms or arrangement of parts described and shown. For example, it is foreseen that various means for advancing the pusher bar relative to the implant holder could be utilized in lieu of the threaded stem and receptacle disclosed herein. Such means could comprise a lever arm, a rack and pinion mechanism or a pneumatic drive mechanism. It is also foreseen that the rod engaging member of the pusher assembly could be of various configurations for example, the pusher bar could only include a single leg having the abutment member extending perpendicular to the leg at a lower end and the connector strut extending perpendicular to the leg at an upper end such that the pusher bar is generally C-shaped with an opening extending from the abutment member to the connector strut to provide access to the head of an implant secured between the associated implant engaging members. Further it is foreseen that in some circumstances that the pusher bar would not need to include a slot or opening for access to the head of an implant secured between the associated implant engaging members. Further it is to be understood that the configuration of the tools of the present invention could be modified to facilitate use with a wide range of osteosynthesis implants and apparatus.

What is claimed and desired to be secured by Letters Patent is as follows:

1. An apparatus for seating a spinal rod in a rod receiving channel in a head of an open ended spinal surgery implant; said apparatus comprising:
   a. an implant holder having a handle portion and an implant engaging portion; said implant engaging portion including opposed implant engaging members for securing one of the implants therebetween;
   b. a receptacle secured to said handle portion and having a threaded bore extending therethrough;
   c. a pusher assembly having a threaded stem rotatably connected to a rod engaging member; said threaded stem being threadingly securable within said threaded bore in said receptacle such that said rod engaging member is advanceable toward and away from an implant secured between said opposed implant engaging members through rotation of said threaded stem;
   d. said implant holder further includes a web having a lower edge which extends transverse to the axis of the rod receiving channel of said implant when said implant is secured between said implant engaging members; and
   e. an opening extends between said lower edge of said web and said head of said implant secured between said implant engaging members.

2. The apparatus as in claim 1 wherein:
   a. said pusher assembly is removably securable to said implant holder.

3. The apparatus as in claim 1 wherein:
   a. said receptacle includes an access slot extending therethrough in communication with said threaded bore; and
   b. a portion of said threaded stem of said pusher assembly is sized for insertion through said access slot.

4. The apparatus as in claim 1 wherein:
   a. said implant holder further includes a pair of guides defining a pair of opposed guide channels through which at least portions of said rod engaging member may be extended for guiding said rod engaging member relative to said implant holder during advancement of said rod engaging member relative to said implant holder.

5. The apparatus as in claim 1 wherein:
   a. a lower surface of said rod engaging member includes a semi-circular rod receiving indent therein adapted to conform to a portion of an outer surface of a spinal rod.

6. The apparatus as in claim 1 wherein:
   a. said implant holder comprises a first arm and a second arm pivotally secured together such that said handle portion comprises an upper portion of said first and second arms and said implant engaging portion comprises a lower portion of said first and second arms.

7. An apparatus for seating a spinal rod in a rod receiving channel in a head of an open ended spinal surgery implant and which permits installation of an implant cap on said head of said open ended spinal surgery implant while maintaining the spinal rod in a seated alignment; said apparatus comprising:

a. an implant holder having a handle portion and an implant engaging portion; said implant engaging portion including opposed implant engaging members for securing said implant therebetween;

b. a pusher assembly including a rod engaging member securable relative to said implant holder such that said rod engaging member is advanceable axially relative to said implant holder toward and away from the implant engaged thereby; said rod engaging member including at least one leg and an abutment member extending perpendicular to said leg at a lower end thereof for engaging a spinal rod and such that an opening extends from above said abutment member toward an upper end of said leg for providing access to an implant secured between said implant engaging members to facilitate installation of a cap thereon;

c. said implant holder further includes a web having a lower edge which extends transverse to the axis of the rod receiving channel of said implant when said implant is secured between said implant engaging members; and d. an opening extends between said lower edge of said web and said head of said implant secured between said implant engaging members.

8. The apparatus as in claim 7 wherein:

a. said implant holder comprises a first arm and a second arm pivotally secured together such that said handle portion comprises an upper portion of said first and second arms and said implant engaging portion comprises a lower portion of said first and second arms.

9. The apparatus as in claim 7 wherein:

a. a receptacle having a threaded bore extending therethrough is mounted on said handle portion of said implant holder; and b. said pusher assembly further comprises a threaded stem rotatably connected to said rod engaging member at an upper end thereof; said threaded stem being threadingly securable within said threaded bore in said receptacle.

10. The apparatus as in claim 9 wherein:

a. said receptacle includes an access slot extending therethrough in communication with said threaded bore; and b. a portion of said threaded stem of said pusher assembly is sized for insertion through said access slot.

11. The apparatus as in claim 7 wherein:

a. said leg of said rod engaging member comprises one of two opposed legs spaced apart by said abutment member at a lower end thereof and defining a slot extending therebetween; said slot sized for insertion of a cap therethrough for installation on an implant secured between said implant engaging members.

12. The apparatus as in claim 11 wherein:

a. said implant holder further includes a pair of guides defining guide channels through which at least portions of said opposed legs of said rod engaging member may be extended.

13. An apparatus for seating a spinal rod in a rod receiving channel in a head of an open ended spinal surgery implant and which permits installation of an implant cap on said head of said open ended spinal surgery implant while maintaining the spinal rod in a seated alignment; said apparatus comprising:

a. an implant holder having a handle portion and an implant engaging portion; said implant engaging portion including opposed engaging members for securing one of the implants therebetween;

b. a receptacle secured to said handle portion and having a threaded bore extending therethrough;

c. a pusher assembly having a threaded stem rotatably connected to a rod engaging member; said threaded stem being threadingly securable within said threaded bore in said receptacle such that said rod engaging member is advanceable toward and away from an implant secured between said implant engaging members through rotation of said threaded stem; said rod engaging member including a pair of opposed legs defining a slot extending therebetween and a cross member extending between said opposed legs at a lower end thereof; said slot being sized for insertion of an implant cap therethrough;

d. a pair of guides secured to said implant holder and defining a pair of rod engaging member receiving channels through which at least portions of said opposed legs of said rod engaging member may be extended; and e. a web having a lower edge extending transverse to the axis of the rod receiving channel of an implant secured between said implant engaging members; an opening extends between said lower edge of said web and said head of said implant secured between said implant engaging members.

14. The apparatus as in claim 13 wherein:

a. said receptacle includes an access slot extending therethrough in communication with said threaded bore; and b. a portion of said threaded stem of said pusher assembly is sized for insertion through said access slot.

15. The apparatus as in claim 13 wherein:

a. said implant holder comprises a first arm and a second arm pivotally secured together such that said handle portion comprises an upper portion of said first and second arms and said implant engaging portion comprises a lower portion of said first and second arms.

16. An apparatus for seating a spinal rod in a rod receiving channel in a head of an open ended spinal surgery implant and which permits installation of an implant cap on said head of said open ended spinal surgery implant while maintaining the spinal rod in a seated alignment; said apparatus comprising:

a. an implant holder comprising a first arm and a second arm pivotally secured together, an upper portion of each of said first and second arms comprising a handle portion and a lower portion of each of said first and second arms comprising an implant engaging member; said implant engaging members pivotally advanceable between an open alignment and a closed alignment for securing one of the implants therebetween;

b. a receptacle secured to said handle portion of one of said first and second arms and having a threaded bore extending therethrough;

c. a pusher assembly having a threaded stem rotatably connected to a rod engaging member; said threaded stem being threadingly securable within said threaded bore in said receptacle such that said rod engaging member is advanceable toward and away from an implant secured between said implant engaging members through rotation of said threaded stem; said rod engaging member including a pair of opposed legs defining a slot extending therebetween and an abutment member extending between said opposed legs at a lower end thereof; said slot being sized for insertion of an implant cap therethrough;

d. a pair of guides secured to said implant holder and defining a pair of guide channels through which at least portions of said opposed legs of said rod engaging member may be extended; and e. a web having a lower edge extending transverse to the axis of the rod receiving channel of an implant secured between said implant engaging members; an opening extends between said lower edge of said web and said head of said implant secured between said implant engaging members.

17. The apparatus as in claim 16 wherein:

a. said receptacle includes an access slot extending therethrough in communication with said threaded bore; and b. a portion of said threaded stem of said pusher assembly is sized for insertion through said access slot.

18. An apparatus for seating a spinal rod in a rod receiving channel in a head of an open ended spinal surgery implant; said apparatus comprising:

a. an implant holder having a handle portion and an implant engaging portion; said implant engaging portion including opposed implant engaging members for securing one of the implants therebetween; and b. a pusher assembly having a rod engaging member and securable to said implant holder such that said rod engaging member is selectively advanceable toward and away from an implant secured between said opposed implant engaging members for seating a spinal rod in the rod receiving channel in the head of the implant secured between said implant engaging members: said rod engaging member including a pair of opposed legs defining a slot extending therebetween and a cross member extending between said opposed legs at a lower end thereof; said slot sized and positioned to permit access to an open end of an implant secured between said opposed implant engaging members.

19. The apparatus as in claim 18 wherein:

a. said implant holder further includes a pair of guides defining guide channels through which at least portions of said opposed legs of said rod engaging member may be extended.

20. An apparatus for seating a spinal rod in a rod receiving channel in a head of an open ended spinal surgery implant; said apparatus comprising:

a. an implant holder having a handle portion and an implant engaging portion; said implant engaging portion including opposed implant engaging members for securing one of the implants therebetween;

b. a pusher assembly having a rod engaging member and securable to said implant holder such that said rod engaging member is selectively advanceable toward and away from an implant secured between said opposed implant engaging members;

c. said implant holder further includes a web having a lower edge which extends transverse to the axis of the rod receiving channel of said implant when said implant is secured between said implant engaging members; and d. an opening extends between said lower edge of said web and said head of said implant secured between said implant engaging members.

* * * * *